United States Patent
Lee et al.

(10) Patent No.: US 11,446,494 B2
(45) Date of Patent: Sep. 20, 2022

(54) SKIN CARE DEVICE AND CONTROL METHOD THEREFOR

(71) Applicant: AMOSENSE CO., LTD, Cheonan-si (KR)

(72) Inventors: Jong Min Lee, Suwon-si (KR); Jun Ho Park, Seoul (KR); Jin-Pyo Park, Seoul (KR); Won-San Na, Seoul (KR)

(73) Assignee: AMOSENSE CO., LTD, Cheonan-si (KR)

( * ) Notice: Subject to any disclaimer, the term of this patent is extended or adjusted under 35 U.S.C. 154(b) by 0 days.

(21) Appl. No.: 16/975,680

(22) PCT Filed: Feb. 13, 2019

(86) PCT No.: PCT/KR2019/001747
§ 371 (c)(1),
(2) Date: Aug. 25, 2020

(87) PCT Pub. No.: WO2019/164173
PCT Pub. Date: Aug. 29, 2019

(65) Prior Publication Data
US 2020/0406036 A1    Dec. 31, 2020

(30) Foreign Application Priority Data
Feb. 26, 2018    (KR) .................. 10-2018-0023199

(51) Int. Cl.
*A61N 1/36*    (2006.01)
*A61N 1/04*    (2006.01)

(52) U.S. Cl.
CPC ....... *A61N 1/36034* (2017.08); *A61N 1/0408* (2013.01)

(58) Field of Classification Search
CPC .... A61N 1/36034; A61N 1/0408; A61N 1/32; A61N 1/322; A61N 1/323; A61N 1/325; A61N 1/326–328; A61N 2005/0644
See application file for complete search history.

(56) References Cited

U.S. PATENT DOCUMENTS 6,183,426 B1    2/2001    Akisada et al.
6,249,706 B1 *  6/2001    Sobota ............... A61N 1/36021
                                                              606/41

(Continued)

FOREIGN PATENT DOCUMENTS

JP    2006-141493 A    6/2006
JP    2017-093522 A    6/2017

(Continued)

OTHER PUBLICATIONS

KR Office Action dated Sep. 30, 2019 as received in Application No. 10-2018-0023199.

(Continued)

*Primary Examiner* — Michael W Kahelin
*Assistant Examiner* — Michael A Rizzuto
(74) *Attorney, Agent, or Firm* — Maschoff Brennan

(57) ABSTRACT

Disclosed are: a skin care device which determines whether, on the basis of a voltage fluctuation according to contact with the skin, the skin care device has been rubbed, and which blocks the output of current through an electrode when rubbing does not occur for at least a set time; and a control method therefor. The disclosed skin care device determines the state of the skin care device on the basis of sensing voltage corresponding to a change in current of a transformation module according to the outputting of alternating current into the skin through contact electrodes, and blocks the output of current of an electrode module if the skin care device is in a fixed state.

13 Claims, 9 Drawing Sheets

(56) References Cited

U.S. PATENT DOCUMENTS

| | | | | |
|---|---|---|---|---|
| 2006/0149337 A1* | 7/2006 | John | ............. | A61N 1/37235 |
| | | | | 607/45 |
| 2008/0262581 A1* | 10/2008 | Barsness | ............ | A61N 1/044 |
| | | | | 607/115 |
| 2009/0204056 A1* | 8/2009 | Nitzan | ............ | A61N 1/0428 |
| | | | | 607/51 |
| 2013/0103017 A1* | 4/2013 | Weckwerth | ......... | A61N 5/0616 |
| | | | | 606/9 |
| 2013/0282085 A1* | 10/2013 | Lischinsky | ........ | A61B 18/1206 |
| | | | | 607/101 |
| 2014/0249522 A1* | 9/2014 | Adanny | ............ | A61N 1/0476 |
| | | | | 606/34 |

FOREIGN PATENT DOCUMENTS

| | | |
|---|---|---|
| KR | 10-2000-0023746 A | 4/2000 |
| KR | 10-2010-0010799 A | 2/2010 |
| KR | 10-2012-0074983 A | 7/2012 |
| KR | 10-2016-0128079 A | 11/2016 |
| KR | 10-2017-0134897 A | 12/2017 |
| KR | 10-1825230 B1 | 2/2018 |

OTHER PUBLICATIONS

KR Decision to Grant dated Apr. 1, 2020 as received in Application No. 10-2018-0023199.

JP Office Action in Application No. 2020-542416 dated Jul. 13, 2021.

\* cited by examiner

[FIG. 1]
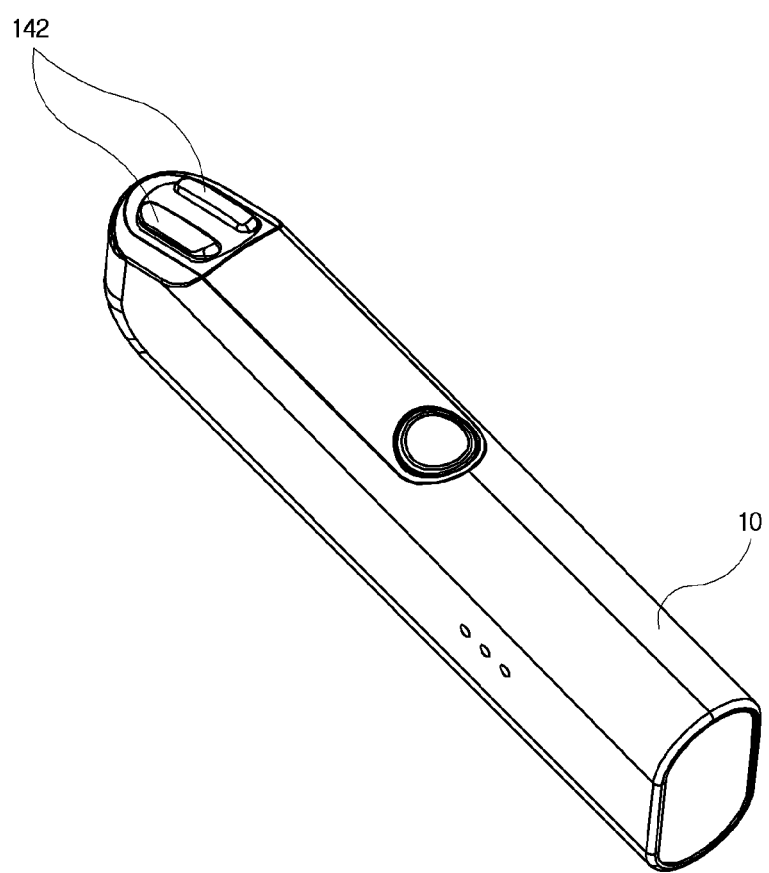

[FIG. 2]
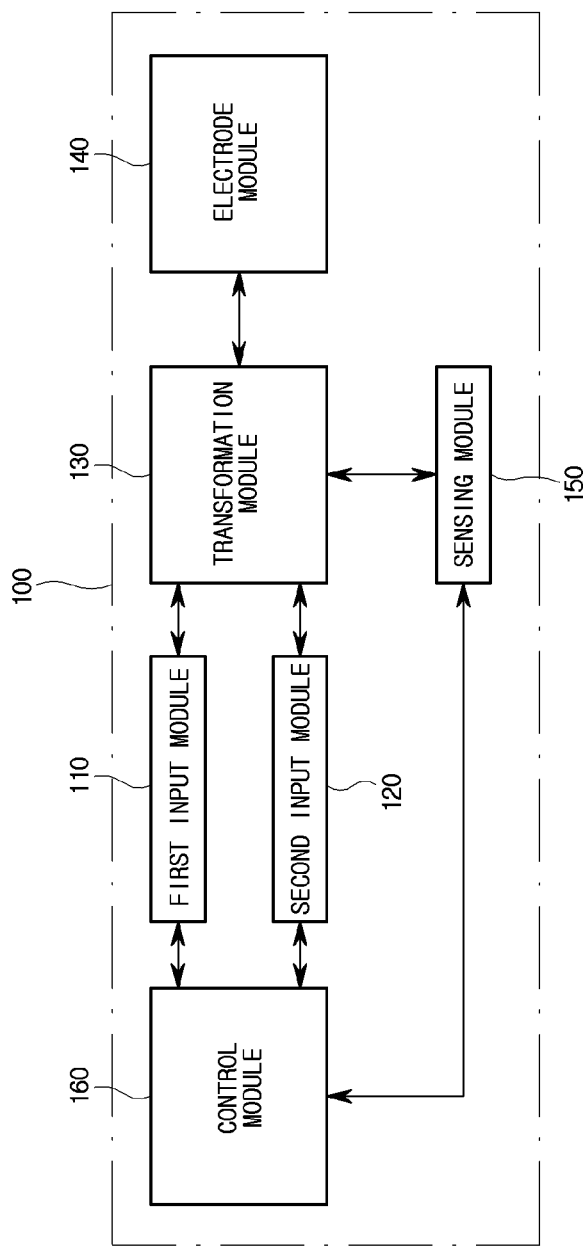

[FIG. 3]
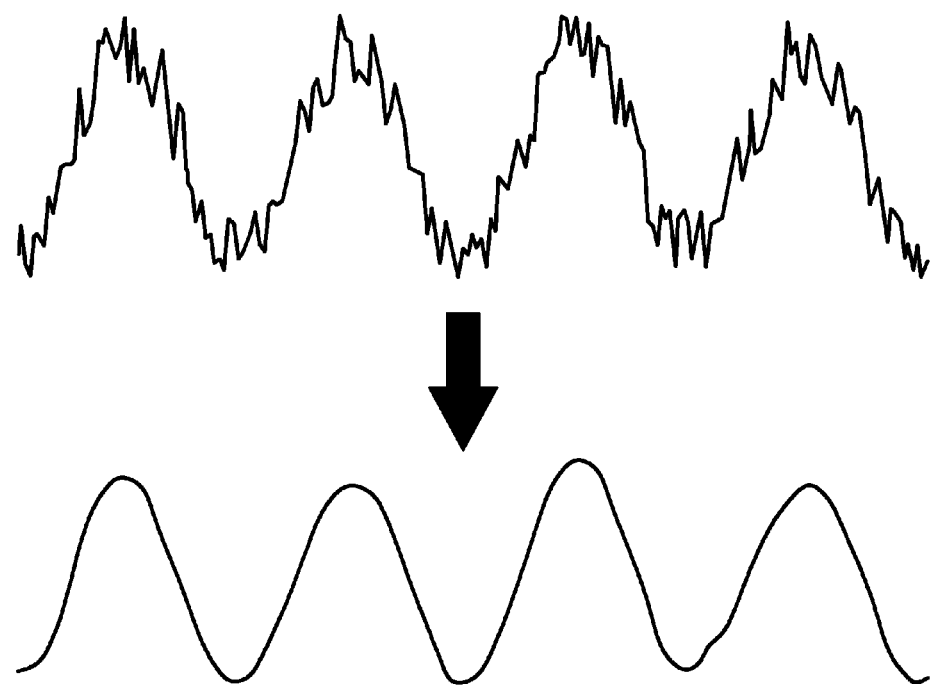

[FIG. 4]
(a)
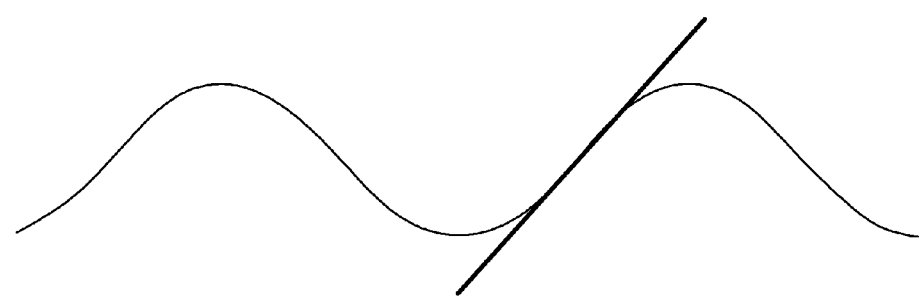
(b)
(c)

[FIG. 5]
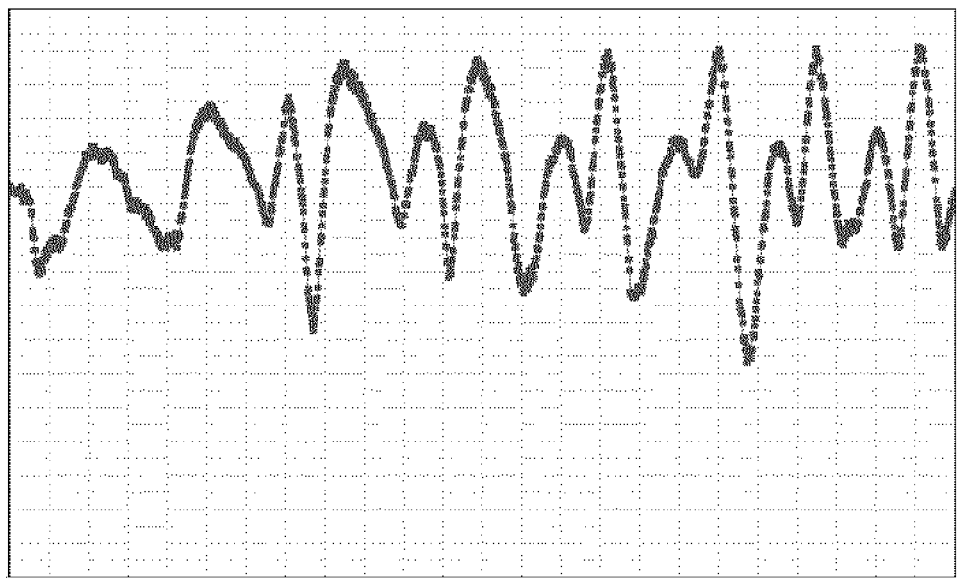
[FIG. 6]
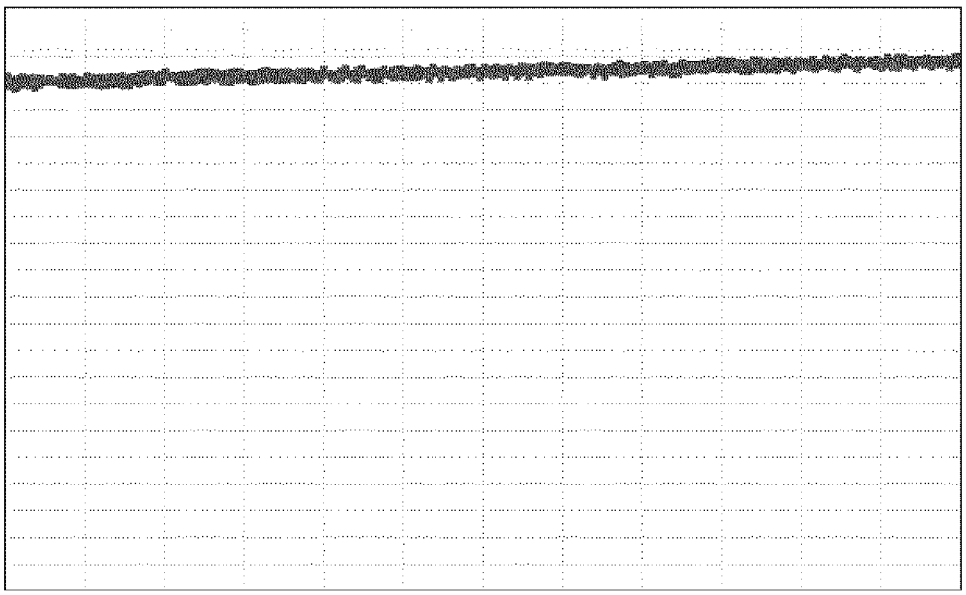

[FIG. 7]
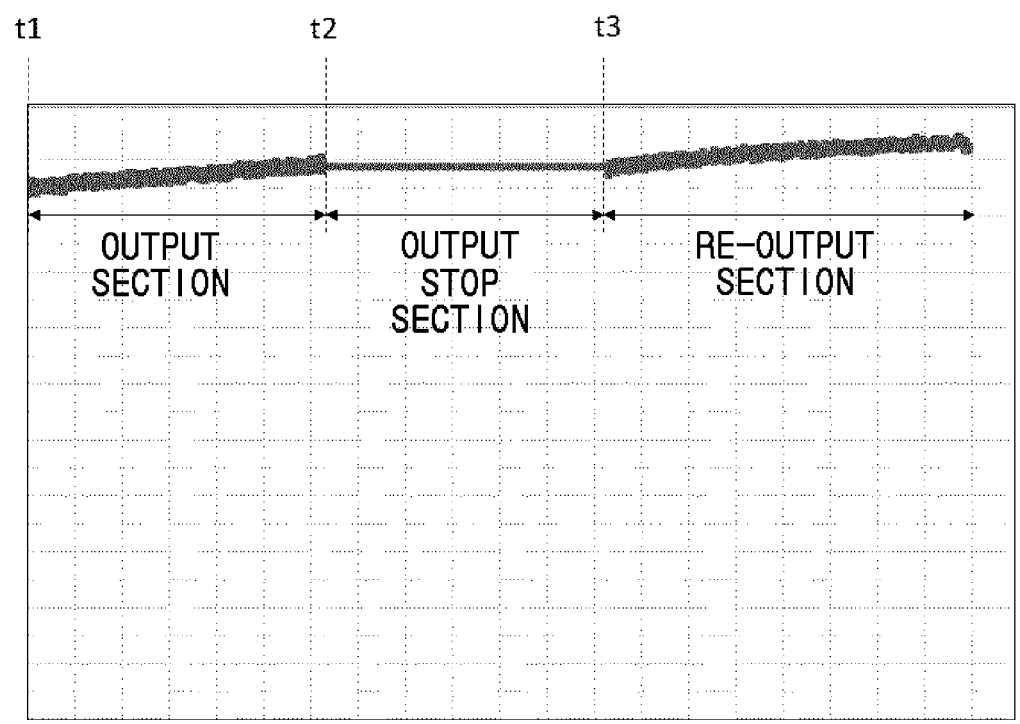

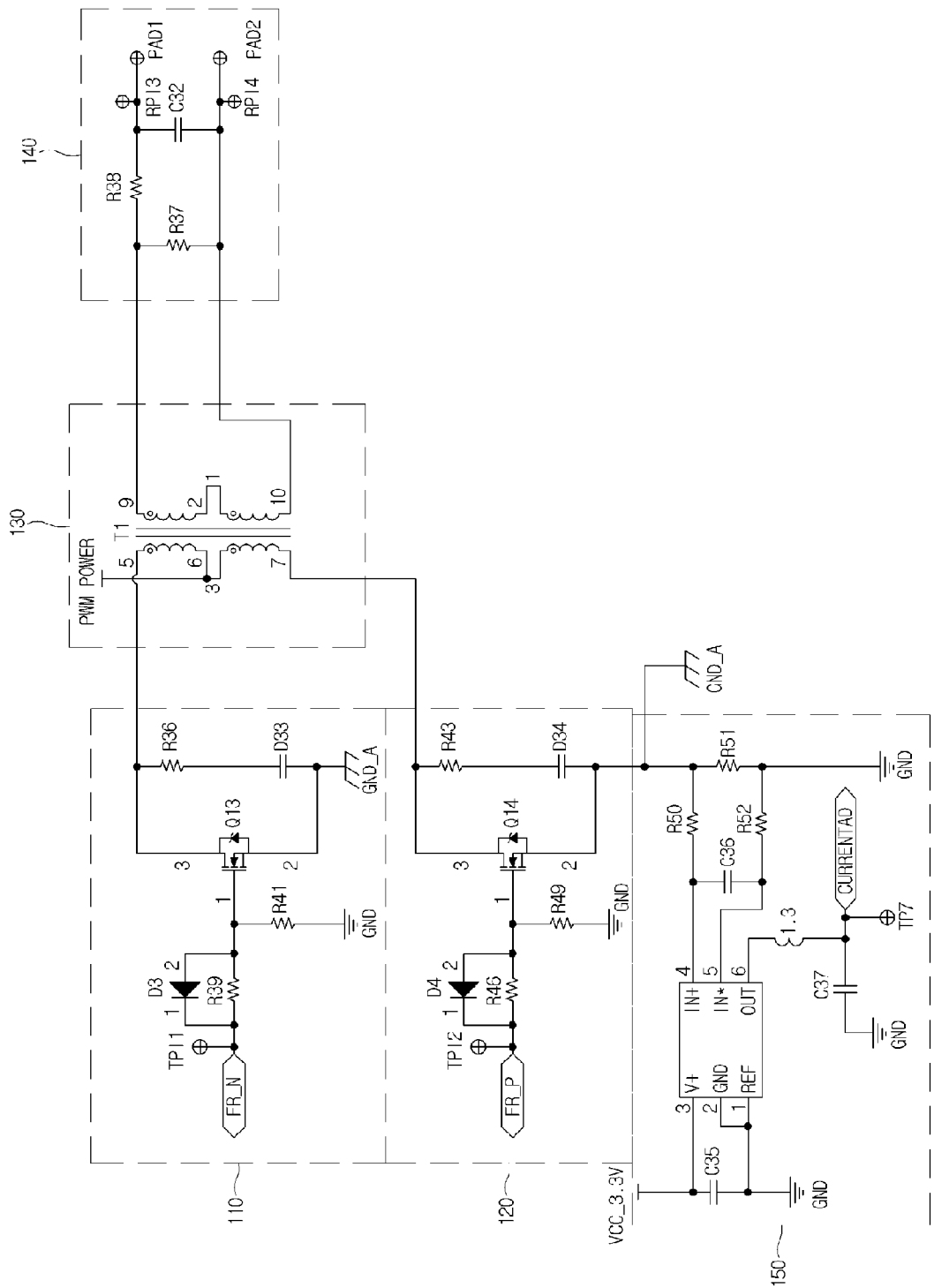
[FIG. 8]

[FIG. 9]
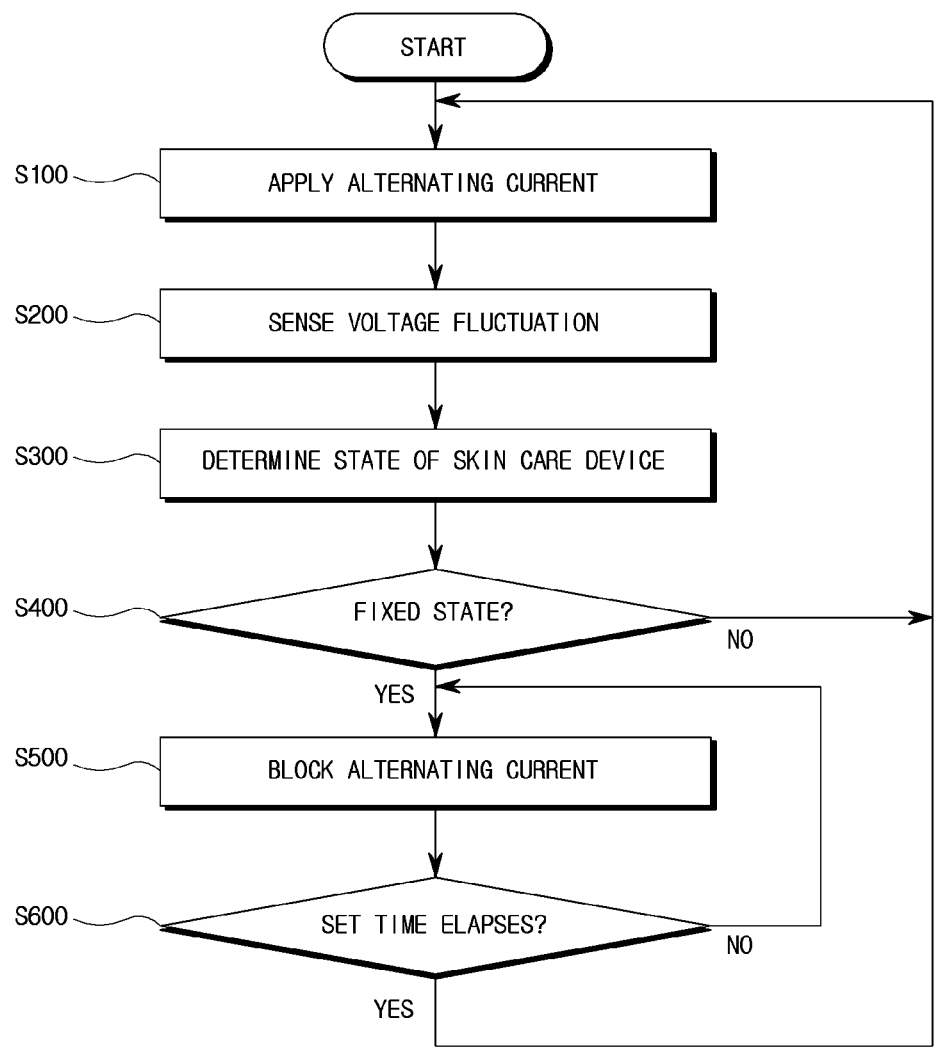

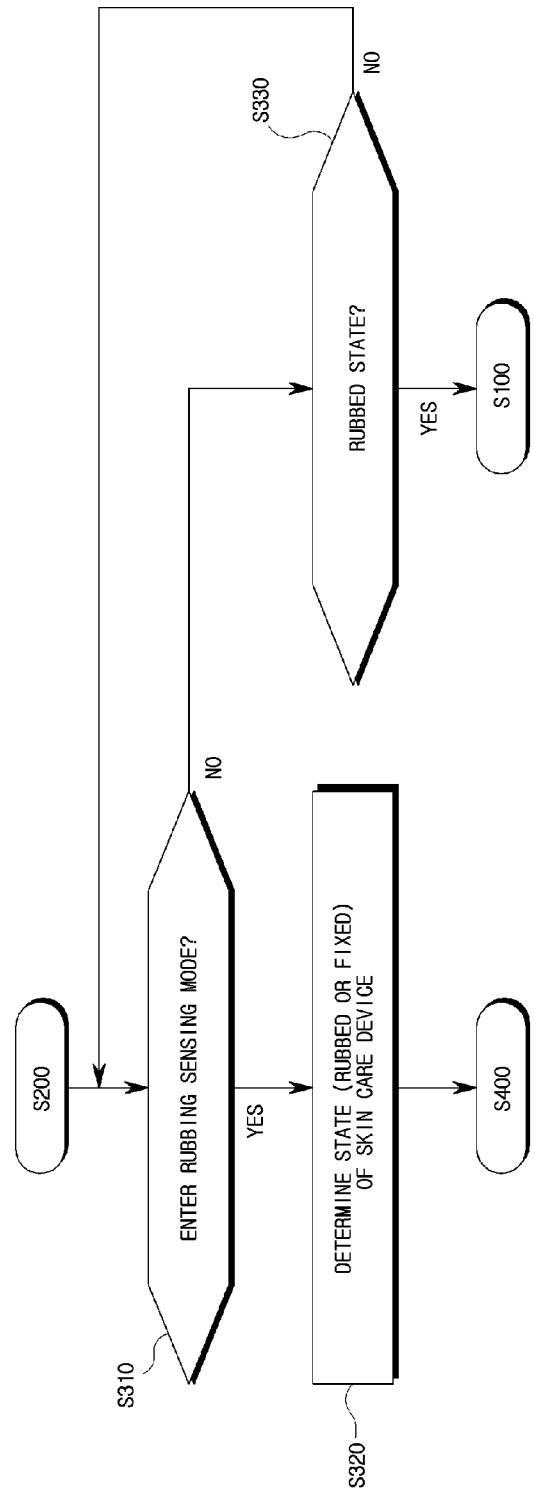
[FIG. 10]

SKIN CARE DEVICE AND CONTROL METHOD THEREFOR

TECHNICAL FIELD

The present disclosure relates to a skin care device and a control method therefor, and more particularly, to a skin care device capable of preventing overheating and a control method therefor.

BACKGROUND ART

Generally, a skin care device may be classified into a skin care device which transfers ultrasound to a user's skin (hereinafter, referred to as an ultrasound type skin care device) and a skin care device which applies a current (hereinafter, a current type skin care device).

The ultrasound type skin care device massages the skin by physical vibrations through ultrasound. The current type skin care device applies an alternating current to the user's skin to remove sebum, waste, or the like or to deeply absorb skin nutrients into the skin.

The current type skin care device applies a current after contacting an electrode to the skin side to be cared to change the electrical environment of the skin, thereby improving the elasticity of the skin, or promoting the absorption of the ampoule applied to the skin.

However, there have been problems in that when the conventional current type skin care device stays in the same position for a certain time or more in an operating state, the temperature of a portion which is in contact with the skin (hereinafter, a contact part) increases excessively, thereby causing the user to feel uncomfortable, or to get minor burns in the skin.

DISCLOSURE

Technical Problem

The present disclosure is proposed to solve the above conventional problems, and an object of the present disclosure is to provide a skin care device and a control method therefor, which determine whether a skin care device is rubbed based on the amount of change in a voltage according to the skin contact, and block a current output through a contact electrode when no rubbing occurs during a set time or more.

Technical Solution

In order to achieve the object, a skin care device according to an exemplary embodiment of the present disclosure determines a state of the skin care device based on a sensed voltage corresponding to a change in a current of a transformation module according to the outputting of an alternating current to a skin through a contact electrode, and blocks a current output of an electrode module when the skin care device is in a fixed state.

The skin care device senses a current at a primary side of the transformation module to convert the current into a sensed voltage, and determines one of a rubbed state and a fixed state as the state of the skin care device based on a fluctuation size of the sensed voltage and a set size. At this time, the skin care device determines that the skin care device is in a rubbed state when the fluctuation size of the sensed voltage is the set size or more, and determines that the skin care device is in the fixed state when the fluctuation size of the sensed voltage is smaller than the set size. The skin care device controls to re-output a current after the set time elapses after blocking the output of the alternating current.

In order to achieve the object, a method for controlling a skin care device according to an exemplary embodiment of the present disclosure applies an alternating current to a skin through a pair of contact electrodes, and blocks the alternating current applied to the skin, when it is determined that the skin care device is in the fixed state based on a voltage fluctuation according to the application of the alternating current.

The method for controlling the skin care device senses a current at a primary side of a transformation module, and converts the current into a sensed voltage to sense the voltage fluctuation. The method for controlling the skin care device determines one of the rubbed state and the fixed state as the state of the skin care device based on the fluctuation size of the sensed voltage and the set size. At this time, the method for controlling the skin care device determines that the skin care device is in the rubbed state when the fluctuation size of the sensed voltage is the set size or more, and determines that the skin care device is in a fixed state when the fluctuation size of the sensed voltage is smaller than the set size. The method for controlling the skin care device re-outputs the alternating current to the skin when the set time elapses after blocking the alternating current.

Advantageous Effects

According to the present disclosure, the skin care device and the control method therefor may determine whether the skin care device is rubbed based on the amount of change in the voltage according to the skin contact, and block the current output through the contact electrode when no rubbing occurs during the set time or more, thereby preventing the burns in the skin which may occur if the contact electrode of the skin care device stays at one place of the skin for a long time.

Further, the skin care device and the control method therefor may measure the varying impedance when the electrode of the skin care device is in contact with the skin without using the temperature sensor for sensing the temperature of the contact part, the proximity sensor for sensing whether to contact the skin or the movement of the skin care device, the gyro sensor, or the like to determine whether the skin care device is rubbed, thereby simplifying the circuitry configuration of the skin care device, and minimizing the manufacturing cost.

DESCRIPTION OF DRAWINGS

FIGS. 1 and 2 are diagrams for explaining a skin care device according to an exemplary embodiment of the present disclosure.

FIGS. 3 to 7 are diagrams for explaining a control module of FIG. 2.

FIG. 8 is a circuit diagram for implementing the skin care device according to an exemplary embodiment of the present disclosure.

FIG. 9 is a flowchart for explaining a method for controlling the skin care device according to an exemplary embodiment of the present disclosure.

FIG. 10 is a flowchart for explaining a step of determining a state of the skin care device in FIG. 9.

MODE FOR INVENTION

Hereinafter, the most preferred exemplary embodiments of the present disclosure will be described with reference to the accompanying drawings in order to specifically describe the exemplary embodiments so that those skilled in the art to which the present disclosure pertains may easily implement the technical spirit of the present disclosure. First, in adding reference numerals to the components of each drawing, it should be noted that the same components have the same reference numerals as much as possible even if they are displayed in different drawings. Further, in describing the present disclosure, when it is determined that the detailed description of the related well-known configuration or function may obscure the gist of the present disclosure, the detailed description thereof will be omitted.

Referring to FIG. 1, a skin care device 100 according to an exemplary embodiment of the present disclosure has a pair of contact electrodes 142 exposed to the outside of a main body. The skin care device 100 applies an alternating current voltage to a skin as the pair of contact electrodes 142 are in contact with the skin. Accordingly, an alternating current flows between the pair of contact electrodes 142 and the skin. Here, the skin care device 100 has been described as having the pair of contact electrodes 142 exposed to the outside, but is not limited thereto and may also be composed of two or more pairs of contact electrodes.

The skin care device 100 senses the fluctuation size (that is, the amount of change) of a voltage according to the alternating current flowing between the contact electrode 142 and the skin. The skin care device 100 determines whether the skin care device 100 is rubbed by comparing the fluctuation size of the voltage with a set size thereof.

The skin care device 100 determines that the skin care device 100 is in the rubbed state to output an alternating current power when the fluctuation size of the voltage is the set size or more. The skin care device 100 determines that the skin care device 100 is in a fixed state to stop the output of the alternating current power when the fluctuation size of the voltage is smaller than the set size. The skin care device 100 re-outputs the alternating current power when a set time elapses after stopping the output of the alternating current power.

To this end, referring to FIG. 2, the skin care device 100 includes a first input module 110, a second input module 120, a transformation module 130, an electrode module 140, a sensing module 150, and a control module 160.

The first input module 110 outputs a first alternating current voltage. The first input module 110 outputs the first alternating current voltage having a cycle. As an example, the first input module 110 outputs the first alternating current voltage having a cycle of about 1 MHz.

The second input module 120 outputs a second alternating current voltage. The second input module 120 outputs the second alternating current voltage having the same cycle as that of the first alternating current voltage. As an example, the second input module 110 outputs the second alternating current voltage having a cycle of about 1 MHz.

The second input module 120 outputs the second alternating current voltage having a phase difference of 180 degrees from the first alternating current voltage which is output from the first input module 110. The second input module 120 outputs the second alternating current voltage having an inverted waveform of the waveform of the first alternating current voltage.

The transformation module 130 sums the alternating current voltages output from the first input module 110 and the second input module 120 to generate a summed alternating current voltage. A primary side of the transformation module 130 is connected to the first input module 110 and the second input module 120. The first alternating current voltage and the second alternating current voltage are input to the transformation module 130 through the primary side. The transformation module 130 sums the first alternating current voltage and the second alternating current voltage to generate the summed alternating current voltage.

The transformation module 130 amplifies the summed alternating current voltage to an output alternating current voltage having a set voltage. The transformation module 130 outputs the output alternating current voltage to the electrode module 140. At this time, a secondary side of the transformation module 130 is connected to the electrode module 140. The transformation module 130 outputs the output alternating current voltage to the electrode module 140 through the secondary side.

The electrode module 140 receives the output alternating current voltage output from the transformation module 130. The electrode module 140 is for improving the elasticity of the skin by generating a potential difference in the user's skin upon input (application) of the output alternating current voltage to change the electrical environment of the skin.

The electrode module 140 includes a pair of contact electrodes 142 which are in contact with the user's skin. The pair of contact electrodes 142 are disposed to be spaced apart from each other on the same surface of the main body. The pair of contact electrodes 142 are implemented in a bi-polar manner.

The pair of contact electrodes 142 implement a function of a known iontophoresis. The pair of contact electrodes 142 configure a closed circuit with the user's skin as the alternating current power is supplied (applied) through the transformation module 130. An alternating current flows through the closed circuit between the pair of contact electrodes 142 and the skin. The alternating current flowing between the pair of contact electrodes 142 and the skin is applied up to a dermal layer of the skin. Accordingly, water molecules in the dermal layer are rotated, thereby preventing the dermal layer from collapsing, and improving the skin wrinkles of the user.

The sensing module 150 senses the amount of current of the transformation module 130. As the alternating current flows between the pair of contact electrodes 142 and the skin, a change in the amount of current occurs at the primary side of the transformation module 130. The amount of current at the primary side of the transformation module 130 is determined in proportion to the current flowing through the secondary side of the transformation module 130. Accordingly, the sensing module 150 is connected to the primary side of the transformation module 130 to sense the current signal. The sensing module 150 converts the current signal into a voltage signal to output the voltage signal. That is, the sensing module 150 converts the current sensed at the primary side of the transformation module 130 into a sensed voltage signal to output the sensed voltage signal.

Meanwhile, referring to FIG. 3, the current signal sensed by the sensing module 150 (that is, the analog current signal) includes a lot of noise. If the noise is included in the current signal, an error (misdetermination) may occur when the control module 160 to be described later determines the state of the skin care device 100.

Accordingly, the sensing module 150 generates a current signal which is refined by filtering the noise from the current signal (hereinafter, the refined current signal). The sensing module 150 filters the signal in a set frequency band from the current signal to generate the refined current signal. As an example, since it is physically impossible for the user to shake the contact electrode 142 20 times or more per second, the sensing module 150 determines the current signal in the frequency band of 20 Hz or more as noise. The sensing module 150 filters the noise (that is, the current signal in the frequency band of 20 Hz or more) from the current signal to generate the refined current signal. The sensing module 150 converts the refined current signal into the sensed voltage signal to output the sensed voltage signal.

The control module 160 determines whether the skin care device 100 enters a rubbing sensing mode based on the sensed voltage signal.

The control module 160 may determine whether the skin care device 100 enters the rubbing sensing mode based on the slope of the sensed voltage signal. The control module 160 calculates the slope of the sensed voltage signal during the set time. The control module 160 determines whether the skin care device 100 enters the rubbing sensing mode by comparing the calculated slope with a set slope (that is, a minimum set slope and a maximum set slope).

As illustrated in FIG. 4A, when the slope of the sensed voltage signal during the set time is the minimum set slope or less, the contact electrode 142 of the skin care device 100 is highly likely to stay at one place of the skin, or to move very slowly.

Accordingly, the control module 160 determines that the skin care device 100 enters the rubbing sensing mode when the slope of the sensed voltage signal during the set time is the minimum set slope or less.

As illustrated in FIG. 4B, when the slope of the sensed voltage signal during the set time exceeds the minimum set slope and is smaller than the maximum set slope, the contact electrode 142 of the skin care device 100 is highly likely to be rubbed normally.

Accordingly, when the slope of the sensed voltage signal during the set time exceeds the minimum set slope and is smaller than the maximum set slope, the control module 160 determines that the skin care device 100 is in a rubbed state without entering the rubbing sensing mode.

As illustrated in FIG. 4C, when the slope of the sensed voltage signal during the set time is the maximum set slope or more, it is determined that there is noise because the rubbing speed may not be generated by the user.

Accordingly, when the slope of the sensed voltage signal during the set time is the maximum set slope or more, the control module 160 determines the corresponding voltage signal as noise to re-determine whether to enter the rubbing sensing mode based on the slope of the sensed voltage signal in a next section without entering the rubbing sensing mode.

Meanwhile, the control module 160 may also determine whether to enter the rubbing sensing mode based on the amplitude of the sensed voltage signal. When the amplitude of the sensed voltage signal smaller than a set amplitude is kept consecutively during the set time or more, the control module 160 determines that the skin care device 100 enters the rubbing sensing mode. At this time, when the amplitude of the sensed voltage signal is the set amplitude or more, the control module 160 determines that the skin care device 100 is in the rubbed state.

When determining that the skin care device 100 enters the rubbing sensing mode, the control module 160 determines the state of the skin care device 100 based on the sensed voltage signal which is output from the sensing module 150. The control module 160 determines one of the rubbed state and the fixed state as the state of the skin care device 100 based on the sensed voltage signal.

Referring to FIG. 5, if the skin care device 100 is rubbed in a state where the pair of contact electrodes 142 are in contact with the user's skin, the sensed voltage signal output from the sensing module 150 has the amount of change (that is, the fluctuation size) of the set size or more.

On the other hand, referring to FIG. 6, if the skin care device 100 is fixed in the state where the pair of contact electrodes 142 are in contact with the user's skin, the sensed voltage signal output from the sensing module 150 has the amount of change smaller than the set size.

Accordingly, the control module 160 determines the state (that is, rubbed or fixed) of the skin care device 100 by comparing the sensed voltage signal with the set size. The control module 160 monitors the fluctuation of the sensed voltage signal. The control module 160 determines the state of the skin care device 100 based on the amount of change in the sensed voltage signal. The control module 160 determines one of the rubbed state and the fixed state as the state of the skin care device 100 based on the amount of change in the sensed voltage signal.

As an example, the control module 160 determines the state of the skin care device 100 based on the amount of change in the sensed voltage signal and the set size. When the amount of change in the sensed voltage signal is the set size or more, the control module 160 determines that the skin care device 100 is in a rubbed state. When the amount of change in the sensed voltage signal is smaller than the set size, the control module 160 determines that the skin care device 100 is in a fixed state.

As another example, the control module 160 may also determine the state of the skin care device 100 based on the number of sensed voltage signals which have the amount of change of the set size or more during a first set time. The control module 160 counts the number of sensed voltage signals having the amount of change of the set size or more during the first set time. When the number of times counted during the first set time is the set number of times or more, the control module 160 determines that the skin care device 100 is in the rubbed state. When the number of times counted during the first set time is smaller than the set number of times, the control module 160 determines that the skin care device 100 is in the fixed state.

As still another example, the control module 160 may also determine the state of the skin care device 100 based on the time during which the amount of change in the sensed voltage signal smaller than the set size during the first set time is sensed. The control module 160 counts the time during which the amount of change in the sensed voltage signal is smaller than the set size. The control module 160 counts the time during which the amount of change in the sensed voltage signal is consecutively smaller than the set size. When the counted time is the first set time or more, the control module 160 determines that the skin care device 100 is in the fixed state. When the counted time is smaller than the first set time, the control module 160 determines that the skin care device 100 is in the rubbed state.

The control module 160 blocks the current output through the pair of contact electrodes 142 based on the state of the skin care device 100. At this time, the control module 160 controls the outputs of the alternating current voltages of the first input module 110 and the second input module 120 according to the state of the skin care device 100.

When determining that the skin care device 100 is in the rubbed state, the control module 160 controls the first input module 110 and the second input module 120 to maintain the output states of the alternating current voltages (that is, the first alternating current voltage and the second alternating current voltage).

When the control module 160 determines that the skin care device 100 is in the fixed state, the control module 160 controls the first input module 110 and the second input module 120 to stop the output of the alternating current voltage. The control module 160 controls the first input module 110 and the second input module 120 to re-output the alternating current voltage when a second set time elapses after stopping the output of the alternating current voltage.

Referring to FIG. 7, since the amount of change in the sensed voltage signal is smaller than the set size during the first set time (t1 to t2), the control module 160 controls the first input module 110 and the second input module 120 to stop the output of the alternating current voltage. The control module 160 maintains the output stop state during the second set time (t2 to t3). The control module 160 controls the first input module 110 and the second input module 120 to re-output the alternating current voltage from the time point during which the second set time elapses (that is, t3).

Meanwhile, when the alternating current voltage is output from the skin care device 100 in a state where the contact electrode 142 is not completely in contact with the skin, a high-frequency alternating current may be instantaneously generated between the contact electrode 142 and the skin to generate spark, thereby causing the user to feel sting due to the spark.

To prevent such a problem, the skin care device 100 may output to the skin a micro alternating current voltage having a relatively low voltage before outputting the high-frequency alternating current voltage to sense whether the contact electrode 142 is in contact with the skin.

As an example, the skin care device 100 outputs the micro alternating current voltage through the contact electrode 142. The pair of contact electrodes 142 configure a closed circuit with the user's skin. The micro alternating current relatively lower than that of when the alternating current voltage is applied through the closed circuit flows between the pair of contact electrodes 142 and the skin.

The skin care device 100 senses whether the contact electrode 142 is in contact with the skin based on the change in the voltage caused by the micro alternating current. The skin care device 100 determines that the contact electrode 142 is in contact with the skin when the sensed voltage caused by the micro alternating current is a set value or more. When it is determined that the contact electrode 142 is in contact with the skin, the skin care device 100 outputs an alternating current through the contact electrode 142.

FIG. 8 is an example of a circuit diagram for implementing the aforementioned skin care device 100.

The first input module 110 is composed of an input terminal RF_N, a plurality of resistors R39, R36, R41, a diode D3, a transistor Q13, and a capacitor C33.

The input terminal RF_N receives the first alternating current voltage from a power source (for example, a battery) of the skin care device 100. One end of the resistor R39 is connected to the input terminal RF_N. The other end of the resistor R39 is connected to a gate of the transistor Q13. At this time, the diode D3 is connected in parallel to the resistor R39. One end of the resistor R41 is connected to a line connecting the other end of the resistor R39 with the transistor Q13, and the other end of the resistor R41 is connected to a ground GND. A drain of the transistor Q13 is connected to the primary side of the transformation module 130. At this time, one end of the resistor R36 is connected to a line connecting the drain of the transistor Q13 with the primary side of the transformation module 130. The other end of the resistor R36 is connected to one end of the capacitor C33. A source of the transistor Q13 and the other end of the capacitor C33 are connected to a ground GND_A.

Here, the plurality of resistors R39, R36, R41, the diode D3, the transistor Q13, and the capacitor C33 which are included in the second input module 120 may be modified in various forms in addition to the connection illustrated in the drawing.

The second input module 120 is composed of an input terminal RF_P, a plurality of resistors R46, R49, R45, a diode D4, a transistor Q14, and a capacitor C34.

The input terminal RF_P receives the second alternating current voltage from the power source (for example, the battery) of the skin care device 100. One end of the resistor R46 is connected to the input terminal RF_P. The other end of the resistor R46 is connected to a gate of the transistor Q14. At this time, the diode D4 is connected in parallel to the resistor R46. One end of the resistor R49 is connected to a line connecting the other end of the resistor R46 with the transistor Q14, and the other end of the resistor R49 is connected to the ground GND. A drain of the transistor Q14 is connected to the primary side of the transformation module 130. At this time, one end of the resistor R45 is connected to a line connecting the drain of the transistor Q14 with the primary side of the transformation module 130. The other end of the resistor R45 is connected to one end of the capacitor C34. A source of the transistor Q14 and the other end of the capacitor C34 are connected to the ground GND_A.

Here, the plurality of resistors R46, R49, R45, the diode D4, the transistor Q14, and the capacitor C34 which are included in the second input module 120 may be modified in various forms in addition to the connection illustrated in the drawing.

The transformation module 130 includes a plurality of coils which are disposed at the primary side and a plurality of coils which are disposed at the secondary side. The plurality of coils disposed at the primary side are connected in series to be connected to the first input module 110 and the second input module 120. The plurality of coils disposed at the secondary side are connected in series to be connected to the electrode module 140.

The electrode module 140 includes a pair of contact electrodes PAD1, PAD2, resistors R37, R38, and a capacitor C32.

The pair of contact electrodes PAD1, PAD2 are connected to the coils disposed at the secondary side of the transformation module 130, respectively. The contact electrode PAD1 is connected to one ends of coils disposed at the secondary side of the transformation module 130, and the contact electrode PAD2 is connected to the other ends of coils disposed at the secondary side of the transformation module 130.

The resistor R38 is disposed on a line connecting the contact electrode PAD1 with the transformation module 130.

One end of the resistor R37 is connected to the line connecting the contact electrode PAD1 with the transformation module 130. At this time, one end of the resistor R37 is connected to the line between the resistor R38 and the transformation module 130. The other end of the resistor R37 is connected to a line connecting the contact electrode PAD2 with the transformation module 130.

One end of the capacitor C32 is connected to the line connecting the contact electrode PAD1 with the transformation module 130. At this time, one end of the capacitor C32 is connected to the line between the resistor R38 and the contact electrode PAD1. The other end of the capacitor C32 is connected to the line connecting the contact electrode PAD2 with the transformation module 130.

Here, the resistors R37, R38 and the capacitor C32 which are included in the electrode module 140 may be modified in various forms in addition to the connection illustrated in the drawing.

The sensing module 150 includes an IC circuit U6. The IC circuit U6 receives an alternating current flowing through the coil at the primary side of the transformation module 130. The IC circuit U6 converts the alternating current into a voltage and then outputs the voltage to the control module 160 through an output terminal Current_AD. Here, resistors R50, R51, R52, capacitors C35, C36, C37, and an inductor L3 which are included in the sensing module 150 may be modified in various forms in addition to the connection illustrated in the drawing.

A method for controlling the skin care device according to an exemplary embodiment of the present disclosure will be described with reference to FIG. 9 as follows.

The skin care device 100 applies the alternating current to the skin which is in contact with the pair of contact electrodes 142 (S100). The skin care device 100 receives the first alternating current voltage and the second alternating current voltage which have waveforms inverted with each other. The skin care device 100 sums the first alternating current voltage and the second alternating current voltage and then amplifies the summed alternating current voltages to the output alternating current voltage having the set voltage to output the output alternating current voltage to the pair of contact electrodes 142. The pair of contact electrodes 142 are applied with the output alternating current voltage in the state which the pair of contact electrodes 142 are in contact with the skin to generate a potential difference in the skin to apply the alternating current to the skin.

The skin care device 100 senses the voltage fluctuation according to the application of the alternating current (S200). The skin care device 100 senses the current signal formed at the primary side of the transformation module 130 as the alternating current is applied to the skin. As the alternating current flows between the pair of contact electrodes 142 and the skin, a change in the amount of current occurs on the primary side of the transformation module 130. The current signal at the primary side of the transformation module 130 is determined in proportion to the current flowing through the secondary side of the transformation module 130. Accordingly, the skin care device 100 is connected to the primary side of the transformation module 130 to sense the current signal. The skin care device 100 converts the sensed current signal to the sensed voltage signal to output the sensed voltage signal.

There may occur an error (misdetermination) in the skin care device 100 upon determining the state in the S300 if noise is included in the current signal. Accordingly, the skin care device 100 generates the refined current signal obtained by filtering the noise from the current signal. The skin care device 100 converts the generated refined current signal into the sensed voltage signal.

The skin care device 100 determines the state of the skin care device 100 based on the voltage fluctuation (S300). The skin care device 100 determines the state of the skin care device 100 based on the sensed voltage signal which is output in the S200. The skin care device 100 determines one of the rubbed state and the fixed state as the state of the skin care device 100 based on the sensed voltage signal.

Referring to FIG. 10, the skin care device 100 determines whether to enter the rubbing sensing mode based on the sensed voltage signal. The skin care device 100 determines whether to enter the rubbing sensing mode based on the slope or the amplitude of the sensed voltage signal.

As an example, the skin care device 100 determines whether to enter the rubbing sensing mode by comparing the slope of the sensed voltage signal during the set time with the set slope. At this time, the skin care device 100 determines that the skin care device 100 enters the rubbing sensing mode when the slope of the sensed voltage signal during the set time is the minimum set slope or less.

As another example, the skin care device 100 may also determine whether to enter the rubbing sensing mode based on the amplitude of the sensed voltage signal. The skin care device 100 determines that the skin care device 100 enters the rubbing sensing mode when the amplitude of the sensed voltage signal which is smaller than the set amplitude is kept consecutively during the set time or more.

When it is determined that the skin care device 100 enters the rubbing sensing mode (S310; YES), the skin care device 100 determines the state (that is, rubbed or fixed) of the skin care device 100 by comparing the sensed voltage signal with the set size (S320). If the skin care device 100 is rubbed in the state where the pair of contact electrodes 142 are in contact with the user's skin, the sensed voltage signal has the amount of change (that is, the fluctuation size) of the set size or more, and if the skin care device 100 is fixed in the state where the pair of contact electrodes 142 are in contact with the user's skin, the sensed voltage signal has the amount of change smaller than the set size.

The skin care device 100 determines the rubbed state based on the amount of change in the sensed voltage signal. To this end, the skin care device 100 monitors the fluctuation of the sensed voltage signal. The skin care device 100 determines the state of the skin care device 100 based on the amount of change in the sensed voltage signal. The skin care device 100 determines one of the rubbed state and the fixed state as the state of the skin care device 100 based on the amount of change in the sensed voltage signal.

As an example, the skin care device 100 determines the state of the skin care device 100 based on the amount of change of the sensed voltage signal and the set size. When the amount of change in the sensed voltage signal is the set size or more, the skin care device 100 determines that the skin care device 100 is in the rubbed state. When the amount of change in the sensed voltage signal is smaller than the set size, the skin care device 100 determines that the skin care device 100 is in the fixed state.

As another example, the skin care device 100 may also determine the state of the skin care device 100 based on the number of sensed voltage signals having the set size or more during the first set time. The skin care device 100 counts the number of sensed voltage signals having the amount of change in the set size or more during the first set time. When the number of times counted during the first set time is the set number of times or more, the skin care device 100 determines that the skin care device 100 is in the rubbed state. When the number of times counted during the first set time is smaller than the set number of times, the skin care device 100 determines that the skin care device 100 is in the fixed state.

As still another example, the skin care device 100 may also determine the state of the skin care device 100 based on the time during which the amount of change in the sensed voltage signal smaller than the set size during the first set time is sensed. The skin care device 100 counts the time during which the amount of change in the sensed voltage signal is smaller than the set size. The skin care device 100 counts the time during which the amount of change in the sensed voltage signal is consecutively smaller than the set size. When the counted time is the first set time or more, the skin care device 100 determines that the skin care device 100 is in the fixed state. When the counted time is smaller than the first set time, the skin care device 100 determines that the skin care device 100 is in the rubbed state. At this time, when the skin care device 100 determines that the skin care device 100 is in the rubbed state, the aforementioned S100 to S300 are repeatedly performed.

The skin care device 100 determines that the skin care device 100 is in the rubbed state without entering the rubbing sensing mode when the slope of the sensed voltage signal during the set time exceeds the minimum set slope and is smaller than the maximum set slope. At this time, the skin care device 100 may also determine that the skin care device 100 is in the rubbed state when the amplitude of the sensed voltage signal is the set amplitude or more.

When it is determined that the skin care device 100 is in the rubbed state (S330; YES), the skin care device 100 moves to the S100 to apply the alternating current to the skin.

Meanwhile, when the slope of the sensed voltage signal during the set time is the maximum set slope or more, the skin care device 100 determines the corresponding voltage signal as noise to select the sensed voltage signal in a next section without entering the rubbing sensing mode. Thereafter, the skin care device 100 re-performs the aforementioned S310 to S330 to re-determine whether to enter the rubbing sensing mode.

When the skin care device 100 is in the fixed state (S400; YES), the skin care device 100 blocks the alternating current applied to the skin (S500). When determining that the skin care device 100 is in the fixed state, the skin care device 100 blocks the inputs of the first alternating current voltage and the second alternating current voltage to block the application of the alternating current to the skin.

When the set time elapses after the alternating current is blocked (S600; YES), the skin care device 100 repeatedly performs the aforementioned S100 to S500.

Meanwhile, the skin care device 100 may apply the micro current to the skin to sense whether to contact the skin and then may perform the S100.

That is, when the alternating current voltage is output from the skin care device 100 in a state where the contact electrode 142 is not completely in contact with the skin, a high-frequency alternating current is instantaneously generated between the contact electrode 142 and the skin to generate spark, thereby causing the user to feel sting due to the spark.

To prevent such a problem, the skin care device 100 may output to the skin the micro alternating current voltage having a relatively low voltage before outputting the high-frequency alternating current voltage to sense whether the contact electrode 142 is in contact with the skin.

As an example, the skin care device 100 outputs the micro alternating current voltage through the contact electrode 142. The pair of contact electrodes 142 configure the closed circuit with the user's skin. The relatively lower micro alternating current than that of when the alternating current voltage is applied through the closed circuit flows between the pair of contact electrodes 142 and the skin.

The skin care device 100 senses whether the contact electrode 142 is in contact with the skin based on the change in the voltage caused by the micro alternating current. The skin care device 100 determines that the contact electrode 142 is in contact with the skin when the sensed voltage due to the micro current is the set value or more. The skin care device 100 performs the S100 when determining that the contact electrode 142 is in contact with the skin.

As described above, although the preferred exemplary embodiment according to the present disclosure has been described, it is understood that changes may be made in various forms, and those skilled in the art may practice various changed examples and modified examples without departing from the claims of the present disclosure.

The invention claimed is:

1. A skin care device comprising:
an electrode module which has at least a pair of contact electrodes configured for outputting an alternating current to a skin;
a transformation module which amplifies an alternating current voltage to be applied to output the amplified alternating current voltage to the electrode module;
a sensing module which senses a current signal of the transformation module, and converts a refined current signal with noise removed from the current signal into a sensed voltage signal to output the sensed voltage signal; and
a control module which determines a state of the skin care device based on the sensed voltage signal output from the sensing module, and controls a current output of the electrode module based on the state of the skin care device,
wherein the control module blocks a current output of the electrode module when the skin care device is in a fixed state,
wherein the control module determines the state of the skin care device based on the sensed voltage signal when determining that the skin care device enters a rubbing sensing mode,
determines that the skin care device is in a rubbed state when a fluctuation size of the sensed voltage signal is a set size or more, and
determines that the skin care device is in a fixed state when the fluctuation size of the sensed voltage signal is smaller than the set size,
wherein the control module determines whether the skin care device enters a rubbing sensing mode based on the sensed voltage signal, and
determines that the skin care device enters the rubbing sensing mode when a slope of the sensed voltage signal is a minimum set slope or less, or an amplitude of the sensed voltage signal is smaller than a set amplitude during a set time, and
wherein the control module determines that there is noise when the slope of the sensed voltage signal during the set time is a maximum set slope or more, and re-determines whether to enter the rubbing sensing mode based on a slope in a next section of the sensed voltage signal.

2. The skin care device of claim 1, comprising:
a first input module which outputs a first alternating current voltage to the transformation module according to a control of the control module; and
a second input module which outputs a second alternating current voltage to the transformation module according to the control of the control module, and
wherein a waveform of the first alternating current voltage is an inverted waveform having a phase difference of 180 degrees from a waveform of the second alternating current voltage.

3. The skin care device of claim 1,
wherein the transformation module sums a first alternating current voltage and a second alternating current voltage which are applied through a primary side to generate a summed alternating current voltage, and amplifies the summed alternating current voltage to an output alternating current voltage having a set voltage.

4. The skin care device of claim 1,
wherein the sensing module filters a signal in a set frequency band or more from the current signal sensed at the primary side of the transformation module to generate the refined current signal.

5. The skin care device of claim 1,
wherein the control module determines that the skin care device is in a rubbed state when the slope of the sensed voltage signal exceeds the minimum set slope and is smaller than a maximum set slope.

6. The skin care device of claim 1,
wherein the control module controls to re-output a current when a set time elapses after blocking the current output of the electrode module.

7. The skin care device of claim 1,
wherein the control module blocks the alternating current voltage applied to the transformation module when determining that the skin care device is in a fixed state, and applies the alternating current voltage to the transformation module when the set time elapses after blocking the alternating current voltage.

8. A method for controlling a skin care device, the method comprising:
applying an alternating current to a skin through at least a pair of contact electrodes;
sensing a voltage fluctuation according to the application of the alternating current;
determining a state of a skin care device based on the voltage fluctuation; and
blocking the alternating current applied to the skin, when it is determined that the skin care device is in a fixed state,
wherein the determining of the state of the skin care device
determines that the skin care device is in a rubbed state when the fluctuation size of the sensed voltage signal converted in the sensing of the voltage fluctuation is a set size or more, and
determines that the skin care device is in a fixed state when the fluctuation size of the sensed voltage signal is smaller than the set size,
wherein the determining of the state of the skin care device comprises determining whether to enter a rubbing sensing mode based on a sensed voltage signal according to the voltage fluctuation,
wherein the determining of whether to enter the rubbing sensing mode determines that the skin care device enters the rubbing sensing mode when a slope of the sensed voltage signal is a minimum set slope or less, or an amplitude of the sensed voltage signal is smaller than a set amplitude during a set time, and
wherein the determining of whether to enter the rubbing sensing mode determines that there is noise when the slope of the sensed voltage signal during the set time is a maximum set slope or more, and re-determines whether to enter the rubbing sensing mode based on a slope in a next section of the sensed voltage signal.

9. The method for controlling the skin care device of claim 8,
wherein the applying of the alternating current comprises applying an amplified output alternating current voltage to the pair of contact electrodes by summing a first alternating current voltage and a second alternating current voltage which have waveforms inverted with each other and then amplifying the summed alternating current voltage to an output alternating current voltage having a set voltage.

10. The method for controlling the skin care device of claim 8,
wherein the sensing of the voltage fluctuation comprises converting a current signal sensed at a primary side of a transformation module into a sensed voltage signal.

11. The method for controlling the skin care device of claim 8,
wherein the sensing of the voltage fluctuation comprises:
generating a refined current signal by filtering a signal in a set frequency band or more from the current signals sensed at a primary side of a transformation module; and
converting the refined current signal into a sensed voltage signal.

12. The method for controlling the skin care device of claim 8,
wherein the determining of whether to enter the rubbing sensing mode determines that the skin care device is in a rubbed state when the slope of the sensed voltage signal exceeds the minimum set slope and is smaller than a maximum set slope.

13. The method for controlling the skin care device of claim 8, further comprising re-outputting an alternating current to the skin when the set time elapses after the blocking of the alternating current applied to the skin.

* * * * *